US008858504B2

(12) United States Patent
Nielsen

(10) Patent No.: US 8,858,504 B2
(45) Date of Patent: Oct. 14, 2014

(54) HAEMOSTATIC VALVE ASSEMBLY

(75) Inventor: Arne Mølgaard Nielsen, Copenhagen (DK)

(73) Assignee: Cook Medical Technologies LLC, Bloomington, IN (US)

(*) Notice: Subject to any disclaimer, the term of this patent is extended or adjusted under 35 U.S.C. 154(b) by 160 days.

(21) Appl. No.: 13/102,632

(22) Filed: May 6, 2011

(65) Prior Publication Data

US 2011/0282301 A1 Nov. 17, 2011

(30) Foreign Application Priority Data

May 11, 2010 (GB) .................................. 1007844.2

(51) Int. Cl.
*A61M 5/178* (2006.01)
*A61M 39/06* (2006.01)

(52) U.S. Cl.
CPC ....... *A61M 39/06* (2013.01); *A61M 2039/0673* (2013.01); *A61M 39/0613* (2013.01); *A61M 2039/062* (2013.01)
USPC .................................. 604/167.01; 604/167.03

(58) Field of Classification Search
USPC .............. 604/167.06, 167.01, 167.03, 164.01
See application file for complete search history.

(56) References Cited

U.S. PATENT DOCUMENTS

| 4,673,393 | A | 6/1987 | Suzuki et al. |
| 5,071,411 | A | 12/1991 | Hillstead |
| 5,176,652 | A | 1/1993 | Littrell |
| 5,391,154 | A | 2/1995 | Young |
| 5,653,697 | A | 8/1997 | Quiachon et al. |
| 6,276,661 | B1 * | 8/2001 | Laird ............................ 251/61.1 |
| 2004/0127853 | A1 | 7/2004 | Howell |
| 2005/0171479 | A1 | 8/2005 | Hruska et al. |
| 2008/0109028 | A1 | 5/2008 | Styre |
| 2009/0118681 | A1 | 5/2009 | Moelgaard Nielsen |
| 2009/0125103 | A1 | 5/2009 | Molgaard-Nielsen |

FOREIGN PATENT DOCUMENTS

| EP | 0538060 A1 | 4/1993 |
| WO | 9911308 A1 | 3/1999 |
| WO | 2009058309 A1 | 5/2009 |
| WO | 2009137163 A1 | 11/2009 |

OTHER PUBLICATIONS

PCT/US2011/035567 International Search Report Aug. 16, 2011 Cook Medical Technologies LLC.
PCT/US2011/035567 Written Opinion Aug. 16, 2011 Cook Medical Technologies LLC.

* cited by examiner

*Primary Examiner* — Kevin C Sirmons
*Assistant Examiner* — Deanna K Hall
(74) *Attorney, Agent, or Firm* — Brinks Gilson & Lione

(57) ABSTRACT

The haemostatic valve assembly (10) includes a housing (14) with a chamber (16) therewithin. A flexible valve element (26) is located in the chamber (16) and supported by the housing (14). A resilient element (21), for example of foam, is located in the chamber (16) and applies a constant closing force on the valve element (26). The valve (10) can be opened by aspirating fluid held within the chamber (16), for example by means of a pump or syringe, thereby to create a vacuum therein which compresses the resilient element (21). Removal of the vacuum allows the resilient element (21) to expand again and to close the valve (10).

20 Claims, 4 Drawing Sheets

HAEMOSTATIC VALVE ASSEMBLY

FIELD OF THE INVENTION

The present invention relates to a haemostatic valve assembly, to an intraluminal introducer, to a deployment device, and to an endoluminal treatment or diagnosis assembly.

BACKGROUND OF THE INVENTION

There are now well established techniques for carrying out endoluminal treatments and diagnoses on a patient. A diagnosis may, for example, involve injection of contrast material and saline solution, A treatment may, for example, involve insertion and deployment of implants or prostheses for carrying out surgical procedures. It may also or in the alternative involve insertion, use and removal of catheters or tools, such as angioplasty or moulding balloons. A treatment may also involve injection of contrast material, saline solution, administration of medicaments and so on. The treatments and diagnoses can be effected within a patient's vascular system, such as arteries or veins. They can also be carried out within other bodily tubes which carry pressurized fluids, examples being the biliary tree and urological system, as well as within an organ, such as the cerebral ventricles and so on.

Endoluminal deployment or treatment devices typically include an elongate catheter assembly having an outer sheath and an internal dilator tip for insertion into the vasculature of a patient up to the deployment or treatment site and into which an elongate treatment or deployment element can be inserted. For example, the sheath may house a catheter or pusher element for carrying a medical device to be implanted into the patient. The sheath may also carry elongate tool elements, catheters for administering medicaments and so on. In the course of such treatments or diagnoses it is important to ensure that the patient does not suffer blood loss through the sheath. For this purpose, it is known to provide at the proximal end of the introducer one or more haemostatic valves in series to close off leakage through the outer sheath.

These haemostatic valves must be such that they allow sliding movement of any delivery or treatment element within the sheath and also for the removal and replacement of such elements. The latter is important, for example, in that many medical procedures may require a plurality of different elements to be passed through the sheath at different times of the procedure for location at a specific position in the patient. Normally, when an exchange of devices takes place, the haemostatic valve has both to seal and allow movement of devices with a diameter up to the inner diameter of the sheath, much smaller devices such as a guide wire typically of 1 mm or so, as well as to seal when the sheath is empty.

Typically, in any one assembly there is provided a variety of valves in light of the difficulties in achieving a reliable seal, all while providing for the removal and replacement of the inserted elements.

Some of these valves are in the form of a disk of elastomeric material located at a proximal end of the sheath and within which there is provided a cut, straight or more commonly Y-shaped, through which an element can be inserted so as to be located within the sheath. As such valves do not provide a complete seal when they hold an insert, typically allowing leakage between the slit and the insert, it is common to use a plurality of such valves disposed in series with one another. These are either at different angular rotations relative to one another or are of different designs, so that collectively they provide a reasonably reliable seal. Typically, there will also be provided one disc with a round hole, optimal for the most-used diameter of a device which passes through that particular sheath. The round disc will give a certain friction, depending upon the need for a forceful seal or to accommodate the size of the actual device passed therethrough.

Examples of such valves can be found, for instance, in U.S. Pat. No. 4,673,393, U.S. Pat. No. 5,176,652 and US-A-2005/017,479.

A difficulty arises with the use of a series of seals, however, in that in order to have good sealing characteristics they also tend to create a significant resistance to movement of an insert, which can substantially impair the operability of the insert by making it too hard to slide within the sheath. This can in some instances lead to damage of the insert, for example by kinking. This risk is particularly acute for inserts which are by necessity very flexible or of a small diameter.

In order to mitigate the above disadvantages, it is also known to use a haemostatic valve which can be opened and closed under the clinician's control. This has the advantage that an element can be inserted into the sheath and moved therealong with relative ease while the controllable haemostatic valve is in an open configuration. Once the insert is in place, the valve can be tightened to effect the seal. Such tightening is also advantageous during the procedure of insertion of the device in the sheath assembly. In practice, it is often necessary for such a structure also to include a valve which self-seals, such as one or more of the disk-shaped valves mentioned above, to ensure sealing during handling.

Such selectively openable and closable valve elements typically have an elongate valve member of tubular form which can be closed by twisting or by application of pressure laterally on the valve element by means of one or more movable closing plates.

Examples of such selectively sealable haemostatic valve assemblies can be found, for example, in U.S. Pat. No. 5,391,154 and U.S. Pat. No. 5,653,697.

A problem with such selectively sealable haemostatic valve assemblies is that they require an additional, controlled, operation to be performed by the clinician during the surgical procedure, that is the opening and closing of the valve element. This can be particularly disadvantageous during any medical procedure, where the clinician is typically required to perform several other tasks. If the valve is not properly closed, there is the risk of leakage of patient fluid through the assembly.

The applicant has previously proposed an improved haemostatic valve assembly, which is the subject of U.S. patent application Ser. No. 12/288,705. The assembly includes a chamber able to be pressurized, an elongate resiliently deformable valve element located within the chamber, a passage through which an elongate element can pass, the valve element being located so as to envelop at least a part of the passage, and means for supplying pressurized fluid to within the chamber, wherein pressurization of the chamber causes the valve element to be biased towards a closed position.

In practice the valve element is biased by the application of fluid pressure to a sealed configuration, at least when an element is located in the valve assembly. The advantage of the system is that the pressurized fluid can provide a reliable seal without requiring a large force to be applied to the seal and thus to any insert held within the valve element. In the case of a generally tubular valve element, the pressure applied to the valve can achieve reliable sealing both when the largest or the smallest inserts are placed therein as well as when any such insert is completely removed from the sheath and the chamber. Since the sealing force need not be large as a result of the substantially constant biasing force applied by the pressurized fluid, the force required to slide inserts through the closed or just sealing valve as it is closed towards the insert valve can be much less than with prior art devices. Furthermore, the pressure may be adjusted to provide an optimum seal at the various sizes of device in use at any particular moment. The source of pressurized fluid includes a syringe coupled to a port of the chamber, a drop bag or a Pressure supplied from the patient's blood stream.

In all of these examples, the chamber can be pressurized at the start of the medical procedure with no further intervention normally being required. Thus, not only can this valve assembly provide a better sealing arrangement but one which is also simpler to implement.

SUMMARY OF THE INVENTION

The present invention seeks to provide an improved haemostatic valve assembly and an improved intraluminal treatment or deployment device.

According to an aspect of the present invention, there is provided a haemostatic valve assembly including: a valve housing; a conformable valve element including an internal passage extending in a longitudinal direction thereof, the valve element being located within the valve housing and being configurable between an open configuration in which the internal passage is open and a sealing configuration in which the internal passage is substantially sealed; a chamber between the housing and the conformable valve element; and a resilient element disposed within the chamber, which biases the conformable valve element towards said sealing configuration; wherein the valve element is responsive to the application of a vacuum to said chamber to compress said resilient element so as to attain said open configuration.

This arrangement of haemostatic valve assembly benefits form the advantageous structure disclosed in the applicant's earlier U.S. patent application Ser. No. 12/288,705 and has the added feature that the valve element has a rest position in which it is sealing. Thus, with no intervention to the assembly, the valve provides a fail safe sealing of the lumen within the sheath. Prior art haemostatic valves tend to be open as they require a mechanism or device to close them (pressure, twisting and so on). Should there be a fault with prior art assemblies, there is the risk that they would remain open and thus that there could be significant loss of bodily fluid through the assembly.

Advantageously, the resilient element is an elastically deformable element. Preferably, the resilient element is a foam element. A foam can provide a soft biasing element which can achieve a good seal in normal conditions and a structure which is porous to allow the aspiration of air or other fluid therein during the application of a vacuum, thereby compressing the foam.

In another embodiment, the resilient element is at least one spring.

The structure is such that the housing and the valve element provide a substantially fluid tight chamber such that on the application of a vacuum to the chamber the valve element is drawn in the direction of the vacuum to compress the resilient element and thus to open the passage in the valve element.

Preferably, the assembly includes a vacuum source coupled to apply a vacuum to said chamber. In the preferred embodiment the vacuum source couples to a port in the housing. In another embodiment, the vacuum source could be coupled to a port in the valve element or any other element forming the walls of the chamber.

The vacuum source could be of a piston type, such as a syringe, a pump or any other suitable vacuum source. A syringe can create a vacuum by pulling out the plunger thereof, with there being provide in some embodiments a mechanism for holding the plunger in an extended position, in cases where friction alone is not considered sufficient.

Advantageously, the valve element includes a valve wall extending in a direction generally longitudinal to the housing. Preferably, the valve element is one of: an hourglass and a cylindrical shape.

A valve element of this type can provide a chamber which is of annular form, the valve element creating what could be said a lumen or bore running along the length of the element and, in the preferred embodiment, of the assembly. This provides an elongate valve element with, as described below, an elongate seal surface for improved sealing. It also provides a structure which is able to interact efficiently with a resilient element in the form of foam, springs and the like.

According to another aspect of the present invention, there is provided a deployment device including a haemostatic valve assembly as specified herein.

According to another aspect of the present invention there is provided a method of operating a haemostatic valve assembly, which assembly is provided with: a valve housing; a conformable valve element including an internal passage extending in a longitudinal direction thereof, the valve element being located within the valve housing and being configurable between an open configuration in which the internal passage is open and a sealing configuration in which the internal passage is substantially sealed; a chamber between the housing and the conformable valve element; and a resilient element disposed within the chamber, which biases the conformable valve element towards said sealing configuration; the method including the steps of: applying a vacuum to the chamber so as to cause the resilient element to be compressed and to open the valve element; releasing said vacuum so as to cause said resilient element to bias said valve element towards said sealing configuration.

According to another aspect of the present invention, there is provided an intravenous treatment assembly including a haemostatic valve assembly as specified herein.

DESCRIPTION OF THE DRAWINGS

Embodiments of the present invention are described below, by way of example only, with reference to the accompanying drawings, in which.

DESCRIPTION OF THE PREFERRED EMBODIMENT

Figure 1:
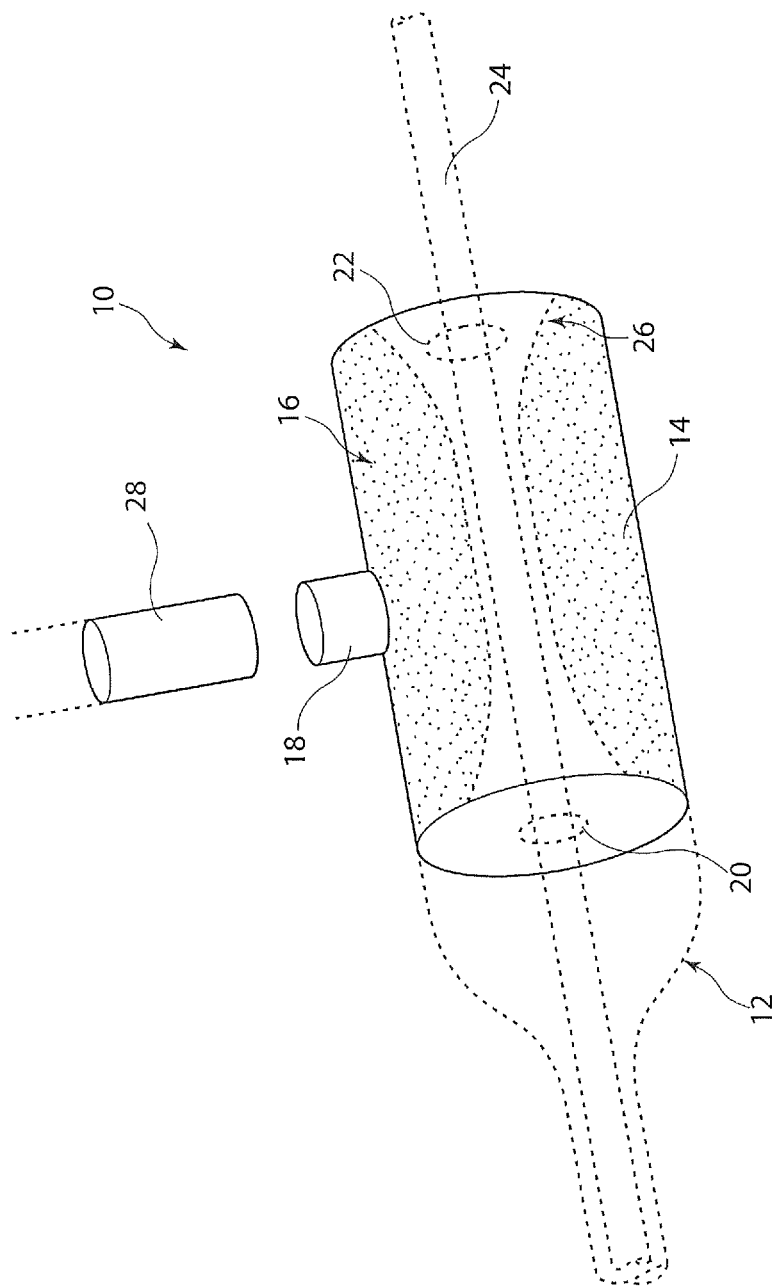
FIG. 1 shows in schematic form a perspective view of an embodiment of haemostatic valve assembly.
Figure 2:
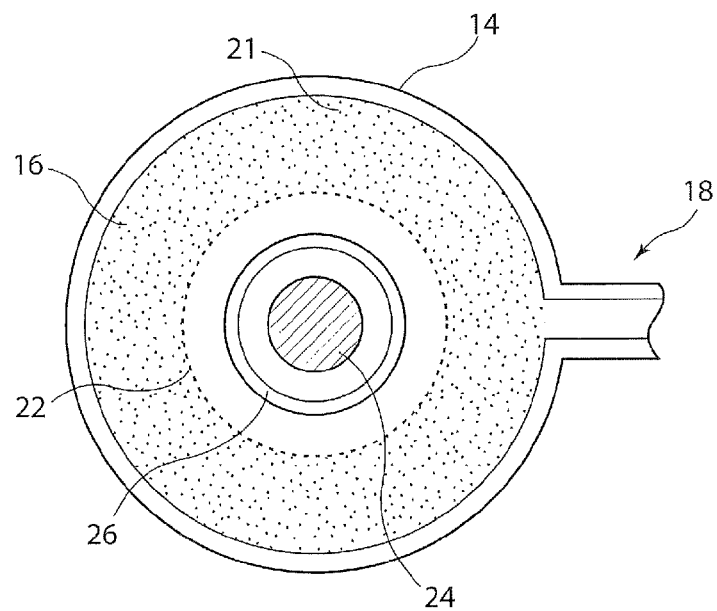
FIG. 2 is a transverse cross-sectional view of the assembly of FIG. 1.

Referring to FIGS. 1 and 2, there is shown in schematic form an embodiment of haemostatic valve assembly 10 which forms part of an introducer or deployment assembly for delivering devices to be inserted into a patient, for carrying out endoluminal placement of implants or for other endoluminal treatments known in the art. The introducer or deployment device could also be of any type designed to effect such delivery, diagnosis or treatments within a patient's organ containing fluids, where sealing during operation is advantageous. Such deployment devices are well known in the art and available, for example, from the applicant, particularly for the deployment of stents, stent grafts, vena cava filters, occlusion devices and so on. There is therefore no need to describe these devices in detail herein.

The valve assembly 10 is designed to couple in a fluid tight manner to a sheath assembly 12 of the deployment device, in a manner similar to existing haemostatic valve assemblies.

The assembly 10 includes a housing 14, preferably translucent, of generally cylindrical form in this embodiment, which provides a chamber 16 therewithin. The shapes of the housing 14 and chamber 16 are not important although it is preferred that they are both generally round in axial cross-section. The housing 14 also includes a port 18 for the application of suction to the chamber 16.

In this embodiment, the housing 14 is provided with circular holes 20, 22 at either end thereof, although again the shape of the holes is not critical. These holes 20, 22 allow for the passage of a catheter or other insert 24 therethrough, one being shown in dotted outline, and are of such a size that they are able to accommodate inserts 24 of the maximum size the sheath 12 can accept.

A flexible valve element 26 is located within the chamber 16 and in this embodiment is supported by the housing 14 at each end thereof. In this embodiment, the valve element 26 is cylindrical and stretched or biased to be of a waisted or hourglass shape. The valve element 26 seals the chamber 16 from the holes 20, 22, thereby providing a passage or lumen from one hole 20 to the other hole 22 which is completely sealed from the chamber 16.

The valve element 26 is fixed to the inner surfaces of the housing 14 by any suitable means including gluing, heat sealing or by any mechanical fastening.

In the preferred embodiment, the valve element can be formed from one or more sheets of a thin compliant material, such as polyurethane, silicone, polychloroprene (Neoprene), styrene butadiene, styrene ethylene butadiene, latex, a rubber or rubberized material.

Within the chamber 16 formed by the housing walls and the valve element, there is provided a resilient element 21 which naturally biases the valve element 26 to a sealing configuration. More specifically, the resilient element 21, using the internal walls of the housing 14 for support, presses against the membrane of the valve element 26 around the whole of, or in some embodiments at least a substantial proportion of, the circumferential extent of the valve element 26, thereby to press the walls of the valve element 26 towards one another so as to close off the passage or lumen running 26 through the assembly. The valve element 26 can close in this manner by virtue of its own resiliency.

In one embodiment, the resilient element 21 is a foam element having a narrow bore running along its length. The foam element is disposed within the annular chamber 16 of the assembly. In another embodiment, the resilient element may include one or more sprung elements which press against the walls of the valve element 26 disposed around the valve element 26 to cause its bore or lumen to constrict. It is also envisaged that the valve element 26 itself could be formed of an elastic material, such as rubber or foam, which tends to close the lumen passing therethrough by adding sealing pressure. Sealing pressure can also be increased by including water or other fluid in the chamber.

The port 18 couples to a vacuum source 28, which may include an aspiration pump for removing air or other fluid held within the chamber 16. The fluid may be water, saline solution, or any other suitable fluid including a gas or any safe air.

Figure 3:
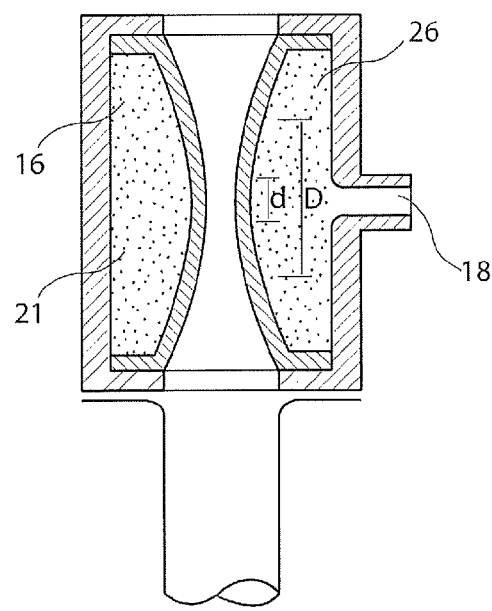
FIG. 3 shows in schematic form the valve and pressurization part of the assembly of FIG. 1.

FIG. 3 shows in schematic form a cross-sectional view in side elevation of the valve assembly 10 of FIGS. 1 and 2 useful in understanding the operation of the valve element 26.

When the valve element is in what could be termed its rest configuration, the biasing element 21 applies a constricting force in all circumferential directions around the leaflet or leaflets of the valve element 26 towards the axial centre of the device 10. This causes the valve element 26 to constrict, particularly at its centre or waist, and thus for this to close the passage 30 which extends between the two end holes 20, 22 in the housing 14. In practice, this biasing force can cause sealing around big or small elements located in the valve, as well as closure of the passage 30 when there is no insert 24 located therewithin. This is achieved by sufficient compression of the walls of the valve element 26 to cause these to attain their sealing configuration. The elasticity of the valve element 26 will enable it to close completely or substantially completely.

In the embodiment of FIGS. 1 to 3, as well as the other embodiments depicted in the other Figures, the valve 26 is located in the housing 14 substantially coaxially with the axis of the holes 20, 22 and is such as to close coaxially around the passage 30.

In practice, there is normally always provided an insert 24 within the valve assembly 10, such as a guide wire, a catheter assembly and the like. The valve element 26 seals against all such inserts, providing a reliable seal both when the insert is introduced as well as during its movement through the valve assembly 10. Moreover, as the seal provided by the pressurized fluid is a much more efficient seal than that provided by prior art systems, it is possible to provide a reliable seal without having to impart a large sealing force against the insert 24. In particular, it will be appreciated that the waist portion of the seal 26 will extend for a significant distance along an insert 24 placed in the valve, which will be greater than the longitudinal sealing extent of a standard flat or pinched valve. Thus, the insert 24 can be fitted through and slid along the valve assembly 10 significantly more easily than with prior art valve structures.

Figure 4:
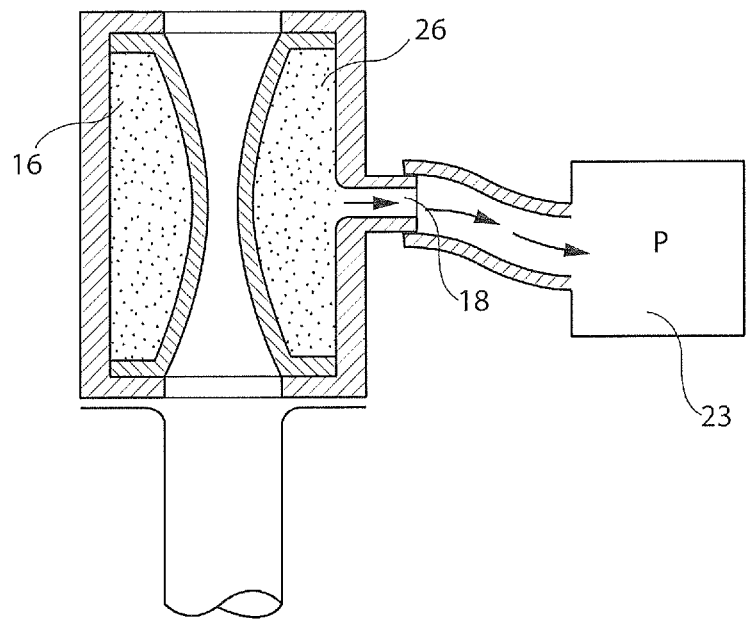
FIG. 4 shows in schematic form an embodiment of assembly which includes a vacuum source in the form of a pump.

Referring to FIG. 4, there is shown an embodiment in which an aspiration pump 23 is coupled to the port 18 for creating a vacuum within the chamber 16. The pump 23 includes a control module, not shown, for allowing a clinician to operate the pump 23 as desired. Such a control may in its simplest form be an on/off switch but it is preferred that there is at least an indicator of the vacuum being generated by the pump 23 and most preferably a device for controlling, advantageously continuously, the level of the vacuum being generated.

In a preferred embodiment, there is provided a simple system, in which there is provided a syringe, such as the syringe 25, coupled to a vacuum chamber which can hold the fluid from the valve. Control of the vacuum can be achieved by detecting leakage in the system, that is when the pressure to create the vacuum is such as to result in leakage in a bleed or other pressure valve.

The pump 23 can be any suitable fluid pump, mains or battery operated, and as suitable pumps are commonplace in the market it is not necessary to detail any particular example herein.

Figure 5:
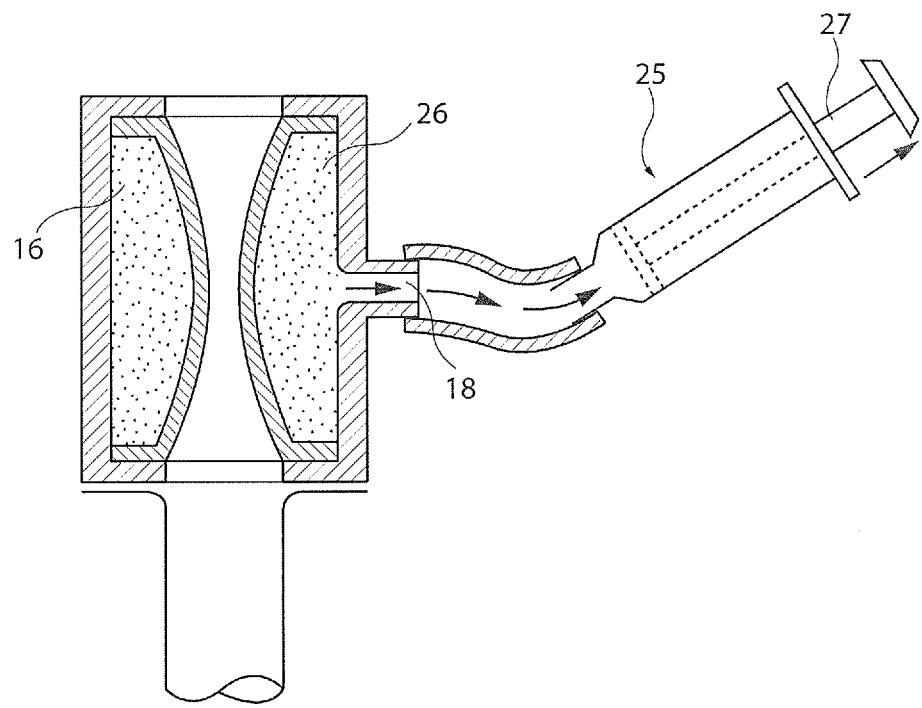
FIG. 5 shows in schematic form another embodiment of assembly which uses a syringe to generate a vacuum.

Referring now to FIG. 5, there is shown another example in which a syringe 25 is coupled to the port 18. The syringe may be any suitable syringe, of sufficient capacity to be able to aspirate enough air or fluid from the chamber 18 so as to be able to open the valve 26. A suitable size can be readily determined by the skilled person. A preferred embodiment provides a vacuum chamber between the syringe 25 and the valve chamber 18.

The syringe preferably includes a mechanism for maintaining a vacuum in the chamber 16, that is with the syringe plunger 27 in an extended position. Such a facility enables the valve to be kept open without having to continue to operate the syringe. A typical holding mechanism may be the friction between the piston seal and the cylindrical wall of the syringe body or may include a specific lock to lock the plunger in an extended position. A preferred embodiment provides a pawl and ratchet mechanism which provides a one-way ratchet function until a ratchet lock is released. As such ratchet mechanisms are well known in the art, they are not described in detail herein.

On the other hand, it may also be desirable to have the plunger remain slidable within the syringe body, such that a vacuum can only be maintained while the plunger is being held manually in an extended position, such that as soon as the plunger is released this will move back into the syringe body as a result of the force of the vacuum, thereby to release the vacuum. The advantage of this arrangement is that the valve 26 will always tend to close and will only open upon the deliberate action to create the vacuum and to maintain it by holding the plunger. As soon as the plunger is released, the resilient element in the valve chamber 26 can again restore the sealing configuration of the valve element 26. Thus, the valve assembly 10 will in its unbiased and unoperated condition always be sealing, rather than open as in prior art arrangements.

In an embodiment, the above described vacuum system could be formed integrally with the valve 10, in particular with the casing 14. That is, a suitable vacuum pump (syringe or other pump) can be formed with the casing such that on holding of the casing the pump is actuated to create the vacuum and open the valve element. This may be by a switch or in another embodiment by compression actuation of the piston of a syringe upon the simple act of holding and pressing on the casing.

In another embodiment, the casing may be compressible to increase the valve sealing pressure, for use for instance in establishing the initial seal.

In use, when it is desired to open the valve 26, for example to insert a catheter or other element therethrough, the clinician will apply a vacuum to the chamber 16, for instance by operation of the pump or syringe. Such operation will aspire the fluid, air or gas within the chamber 16 and cause the resilient element 21 to be compressed by the wall of the valve element 26, which is being drawn to the chamber walls by the generated vacuum, thereby to open the passage through the valve element 26. Once opened, the catheter or other element can be easily inserted through the valve assembly.

The valve 26 can be closed again by releasing the vacuum, for instance by reverse operation of the pump, syringe or by opening a bleed valve (not shown) in the port 18, thereby to allow fluid to flow back into the chamber 18 thereby restoring pressure therein. It is the restorative biasing force of the resilient element 21 which biases the valve element 26 to a sealed configuration, rather that any mechanism such as pump pressure or other mechanical closing device. Thus, with no vacuum applied in the chamber 16, the valve will be biased closed.

Therefore, as will be apparent, the valve is normally in a closed configuration, achieved automatically by the resilient element. Should there be any defect in operation or control by a clinician, therefore, the valve will close rather than remain open.

It will be apparent that the resilient element 21 occupies only a part of the space of the chamber 16, so as to allow the other part to be filled with air or other fluid. It is the pressure of this air or other fluid which can act to provide the necessary vacuum and force to compress the resilient element 21.

It is preferred that the surgeon is provided with the ability to regulate pressure inside the chamber 16 and therefore the sealing pressure of the valve element 26. This can be achieved in its simplest form by tactile sensation on a syringe plunger. In another embodiment, the system may be provided with a pressure meter, which could be provided within the assembly 10 but which in another embodiment is provided as a separate element coupled within the fluid aspiration path.

It is preferred that the resilient element 21 is able to close off the valve 26 completely in the absence of a vacuum. However, in some embodiments the resilient element may keep the valve element 26 at a minimum aperture, which aperture is preferably small enough to prevent any significant leakage of fluid from within a patient. In this regard, in use there is always likely to be a guide wire or small catheter located within the valve element. It will be appreciated that the closure of the valve 26 will, in the case of an elastic valve element 26, be a function of the stretch force produced by the walls of the valve element and the biasing force produced by the resilient element 21.

In addition to providing a fail safe condition in which the valve 10 is closed, the arrangement taught herein provides a constant and reliable sealing force on the valve by virtue of the restorative force produced by the resilient element 21. Thus, when the vacuum is released, the valve will close and remain closed without the need for any intervention by the clinician.

FIGS. 1, 2 and 3 show a flexible valve element which extends continuously from one end of the casing 14 to the other, in effect completely sealing the chamber 16 from the passage between the holes 20, 22.

Figure 6:
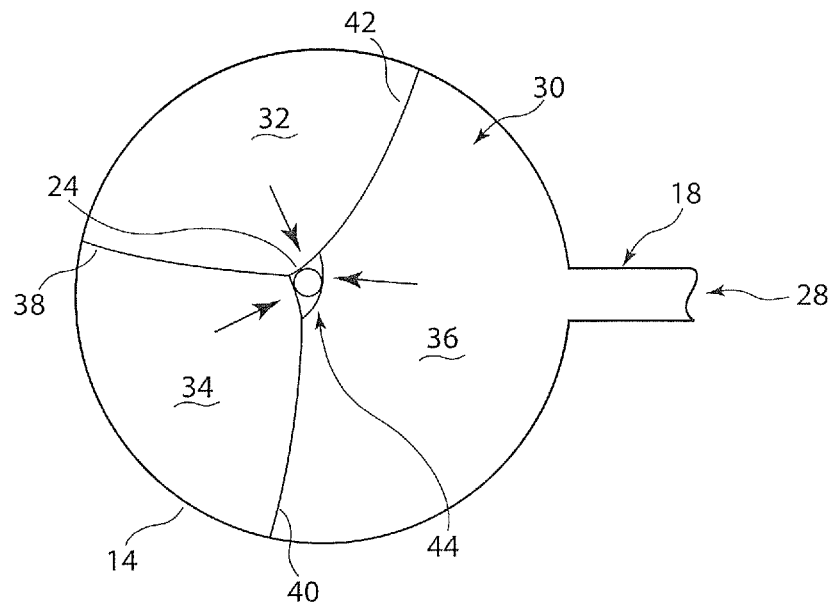
FIG. 6 shows a plan view of an embodiment of tri-leaflet valve element.

FIG. 6 shows in plan view an embodiment of valve structure useful for any of the valves shown in FIGS. 1 to 5 or any other valve configuration having the characteristics of the valves of those Figures. FIG. 6 shows valve element 30 being formed of three leaflets 32, 34 and 36. These are in effect elongate sheets of valve material which are sealed to one another at longitudinal seals 38, 40 and 42, thereby to create a valve element 30 having the general hourglass shape shown in the preceding Figures. The three valve material sheets are sealed against the housing 14 to make a tight connection to the holes 20 and 22. As can be seen in the plan view of FIG. 6, this structure of valve element 30 provides a triangular passage 44 through the valve element 30 and thus through the valve assembly. The advantage of this structure, it has been found, is that when pressure is applied to close the valve element 30, as shown by the arrows in FIG. 6, the three leaflets are able to close more tightly around the insert 24 than a valve element having, for example, two leaflets. Moreover, when compared to a valve element formed of a single leaflet, when a tri-leaflet valve element of the type shown in FIG. 8 is in its non pressurized state, there remains little contact between the leaflets 32-36 of the valve element 30 and the insert 24, thereby reducing any friction between these two components. This thus facilitates the movement of the element 24 through the valve assembly 10 which is, of course, an important advantage with deployment devices of the type contemplated in this application.

The embodiment of FIG. 6 can have any of the features of the valve elements shown in the preceding Figures. It is also envisaged in some embodiments that the valve element 30 may only have a tri-leaflet structure part way along its length, that is at its central portion.

Figure 7:
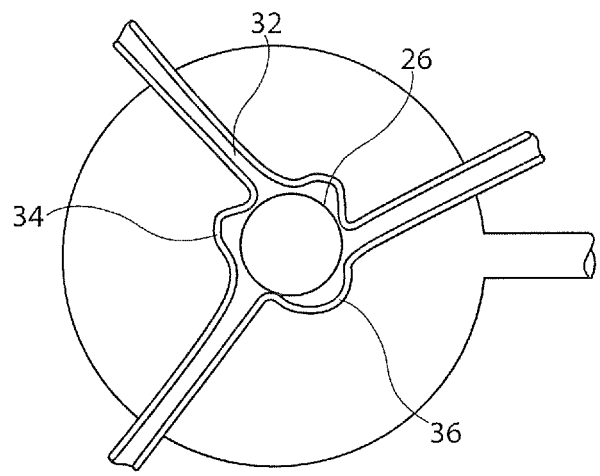
FIG. 7 shows the valve element of FIG. 6 in a sealed state.

In operation, the three leaflets 32-36 would come in sealing contact with one another by folding over themselves and/or over one another, as can be seen in FIG. 7.

Further details of a suitable structure for this tri-leaflet valve of FIGS. 6 and 7 can be found in the Applicant's copending U.S. Provisional patent application No. 60/001,019 filed on 30 Oct. 2008 and the United States Utility patent application claiming priority therefrom.

It is envisaged that this tri-leaflet valve element 30 could be pretwisted, for example during manufacture, which can assist in its closure.

As disclosed herein, in place or in addition to a resilient element such as foam, there could be provided around the valve element at least one spring for applying a closing pressure on the valve element. This embodiment would function in a similar manner to the preferred embodiment described, that is to open upon the application of a vacuum within the chamber 16.

The systems taught herein can provide a much enhanced sealing function compared to prior art systems. Furthermore, as a result of this the valve element does not have to be formed of a compliant material as with existing haemostatic valves. The valve element could equally be formed of a relatively non-compliant material, such as a material commonly used for endovascular balloons, for example polyethylene terephathalate (PET), polyethylene, nylon, PVC, or any other known materials. An advantage of non-compliant materials of this type is that they can be very flexible and have lower coefficients of friction compared to compliant materials.

What is claimed is:

1. A haemostatic valve assembly including:
   a valve housing including a first and a second hole:
   a conformable valve element located within the valve housing and including at least one elongate seal surface defining an internal passage extending in a longitudinal direction between the first and the second hole of the valve housing, the valve element configurable between an open configuration in which the internal passage is open and a sealing configuration in which the internal passage is substantially sealed;
   a chamber between the housing and the conformable valve element;
   a resilient element disposed and remaining within the chamber, which biases the conformable valve element towards said sealing configuration;
   wherein the valve element seals the chamber from the first and the second hole; and
   wherein the valve element is responsive to the application of a vacuum to the chamber to compress said resilient element so as to attain said open configuration, and in the absence of the application of a vacuum the resilient element causes the internal passage to be substantially sealed.

2. A haemostatic valve assembly according to claim 1, where the resilient element is an elastically deformable element.

3. A haemostatic valve assembly according to claim 2, wherein the resilient element is a foam element.

4. A haemostatic valve according to claim 2, wherein the resilient element is a at least one spring.

5. A haemostatic valve assembly according to claim 1, including a vacuum source coupled to apply a vacuum to said chamber.

6. A haemostatic valve assembly according to claim 1, wherein the valve element includes a valve wall extending in a direction generally longitudinal to the housing.

7. A haemostatic valve assembly according to claim 1, wherein the valve element is one of: an hourglass and a cylindrical shape.

8. A haemostatic valve assembly according to claim 1, wherein the valve element extends substantially along the entirety of a longitudinal extent of the chamber.

9. A haemostatic valve assembly according to claim 6, wherein the valve element is fluid tight to the chamber.

10. A haemostatic valve assembly according to claim 1, wherein the valve element has a multi-leaflet form.

11. A deployment device including a haemostatic valve assembly according to claim 1.

12. A haemostatic valve assembly according to claim 2, including a vacuum source coupled to apply a vacuum to said chamber.

13. A haemostatic valve assembly according to claim 2, wherein the valve element includes a valve wall extending in a direction generally longitudinal to the housing.

14. A haemostatic valve assembly according to claim 2, wherein the valve element is one of: an hourglass and a cylindrical shape.

15. A haemostatic valve assembly according to claim 2, wherein the valve element extends substantially along the entirety of a longitudinal extent of the chamber.

16. A haemostatic valve assembly according to claim 2, wherein the valve element is fluid tight to the chamber.

17. A haemostatic valve assembly according to claim 2, wherein the valve element has a multi-leaflet form.

18. A deployment device including a haemostatic valve assembly according to claim 2.

19. A method of operating a haemostatic valve assembly, which assembly is provided with: a valve housing including a first and a second hole; a conformable valve element located within the valve housing and including at least one elongate seal surface defining an internal passage extending in a longitudinal direction between the first and the second hole of the valve housing, the valve element configurable between an open configuration in which the internal passage is open and a sealing configuration in which the internal passage is substantially sealed; a chamber between the housing and the conformable valve element; and a resilient element disposed and remaining within the chamber, which biases the conformable valve element towards said sealing configuration; wherein the valve element seals the chamber from the first and second hole;
   the method including the steps of:
   applying a vacuum to the chamber so as to cause the resilient element to be compressed and to open the valve element;
   releasing said vacuum so as to the cause the resilient element to bias the valve element towards the sealing configuration, wherein in the absence of the application of a vacuum the resilient element causes the internal passage to be substantially sealed.

20. A method according to claim 19, including the step of inserting or removing an elongate element into the valve assembly when said vacuum is applied.

* * * * *